United States Patent
Avni (10) Patent No.: US 10,105,505 B2
(45) Date of Patent: Oct. 23, 2018

(54) MEANS AND METHOD FOR FLUID PULSES

(71) Applicant: Respinova Ltd., Herzliya Pituach (IL)

(72) Inventor: Yuval Avni, Tel Aviv (IL)

(73) Assignee: RESPINOVA LTD., Herzliya Pituach (IL)

( * ) Notice: Subject to any disclaimer, the term of this patent is extended or adjusted under 35 U.S.C. 154(b) by 321 days.

(21) Appl. No.: 14/726,886

(22) Filed: Jun. 1, 2015

(65) Prior Publication Data

US 2015/0265788 A1 Sep. 24, 2015

Related U.S. Application Data (63) Continuation-in-part of application No. 13/377,087, filed on Jan. 13, 2012, now Pat. No. 9,114,224.

(Continued)

(51) Int. Cl.
*A61M 16/08* (2006.01)
*A61M 16/00* (2006.01)
(Continued)

(52) U.S. Cl.
CPC ........ *A61M 16/0066* (2013.01); *A61M 11/02* (2013.01); *A61M 15/00* (2013.01);
(Continued)

(58) Field of Classification Search
CPC ............ A61B 18/1206; A61B 18/1477; A61B 18/1492; A61B 18/18; A61B 18/1815; A61B 18/24; A61B 2017/00022; A61B 2018/00011; A61B 2018/00023; A61B 2018/00214; A61B 2018/0022; A61B 2018/00541; A61B 2018/00577; A61B 2018/0212; A61B 2018/143; A61B 2018/1432; A61B 2018/1861; A61B 8/12; A61H 15/0085; A61H 2201/0157;
(Continued)

(56) References Cited

U.S. PATENT DOCUMENTS

| 5,211,171 A | 5/1993 | Choromokos |
| 5,603,315 A | 2/1997 | Sasso, Jr. |

(Continued)

OTHER PUBLICATIONS

Israeli Patent Office, "International Search Report and Written Opinion dated Feb. 4, 2010 in corresponding International Application No. PCT/IL2009/000962", Feb. 4, 2010, Israel.

(Continued)

*Primary Examiner* — Annette Dixon (57) ABSTRACT

A pulsating therapeutic inhaler generating pneumatic pulses for treating respiratory disorders. The inhaler includes: a linear passage that has an elongate axis and is configured to conduct a fluid flow in a laminar manner; a patient interface fluidly connectable to the patient's respiratory tract having an aperture fluidly connectable to the passage; and a shutter disposed between the passage and the aperture configured to modulate a fluid pressure within the fluid flow. The shutter includes a disc having at least one cutout and rotating about an axis parallel to the passage axis. The cutout has four cornered perimeter thereof with two side portions and two circumferential arcs configured relative to the rotation axis. The side portions are circumferentially anti-symmetrical relative to the aperture.

24 Claims, 11 Drawing Sheets

Related U.S. Application Data (60) Provisional application No. 62/006,292, filed on Jun. 2, 2014.

(51) Int. Cl.
*A61M 11/02* (2006.01)
*A61M 15/00* (2006.01)

(52) U.S. Cl.
CPC ...... *A61M 16/0006* (2014.02); *A61M 16/021* (2017.08); *A61M 15/0005* (2014.02); *A61M 16/0866* (2014.02); *A61M 2205/07* (2013.01); *A61M 2205/103* (2013.01)

(58) Field of Classification Search
CPC .... A61H 2201/0165; A61H 2201/0192; A61H 2201/0207; A61H 2201/0214; A61H 2201/0285; A61H 2201/105; A61H 2201/1215; A61H 2201/1604; A61H 2201/1607; A61H 2201/165; A61H 2205/023; A61H 2205/024; A61H 2205/025; A61H 2205/08; A61H 23/00; A61H 23/0254; A61H 9/0078; A61M 1/0066; A61M 11/005; A61M 11/007; A61M 11/02; A61M 11/042; A61M 11/06; A61M 15/00; A61M 15/0003; A61M 15/0016; A61M 15/0018; A61M 15/002; A61M 15/0035; A61M 15/0065; A61M 15/0085; A61M 15/0086; A61M 15/009; A61M 15/02; A61M 15/08; A61M 16/00; A61M 16/0006; A61M 16/0009; A61M 16/0051; A61M 16/0057; A61M 16/0063; A61M 16/0066; A61M 16/0069; A61M 16/0096; A61M 16/0833; A61M 16/0858; A61M 16/0866; A61M 16/1015; A61M 16/1055; A61M 16/106; A61M 16/107; A61M 16/1075; A61M 16/12; A61M 16/125; A61M 16/16; A61M 16/20; A61M 16/202; A61M 16/205; A61M 16/206; A61M 16/208; A61M 2016/0021; A61M 2016/0027; A61M 2016/0036; A61M 2016/0039; A61M 2016/0042; A61M 2016/1025; A61M 2016/103; A61M 2016/1035; A61M 2021/0088; A61M 21/02; A61M 2202/0208; A61M 2202/0275; A61M 2202/064; A61M 2205/07; A61M 2205/103; A61M 2205/106; A61M 2205/16; A61M 2205/18; A61M 2205/3331; A61M 2205/3365; A61M 2205/3561; A61M 2205/3569; A61M 2205/3592; A61M 2205/42; A61M 2205/50; A61M 2205/502; A61M 2205/52; A61M 2205/581; A61M 2205/587; A61M 2205/6018; A61M 2205/6045; A61M 2205/6054; A61M 2205/70; A61M 2205/8206; A61M 2205/8212; A61M 2209/084; A61M 2210/0618; A61M 2230/04; A61M 2230/205; A61M 2230/30; A61M 2230/432; A61M 2230/435; A61M 2230/46; A61N 7/022; F16K 11/076; G01F 1/40; G01F 1/42; Y10T 137/2544
USPC ............ 128/200.14, 200.21, 200.22, 203.12, 128/203.15, 203.26, 204.18, 204.19, 128/204.21, 204.23, 204.25, 204.26, 128/205.19, 205.24
See application file for complete search history.

(56) References Cited

U.S. PATENT DOCUMENTS

| | | | |
|---|---|---|---|
| 5,862,802 A | 1/1999 | Bird | |
| 5,931,163 A * | 8/1999 | Stegmann | A61M 16/20 128/204.18 |
| 6,415,797 B1 | 7/2002 | Groth et al. | |
| 6,581,596 B1 * | 6/2003 | Truitt | A61M 16/00 128/204.18 |
| 6,934,571 B2 | 8/2005 | Weismann et al. | |
| 7,165,547 B2 | 1/2007 | Truitt et al. | |
| 7,270,638 B2 | 9/2007 | Lundberg et al. | |
| 7,314,046 B2 | 1/2008 | Schroeder et al. | |
| 8,051,854 B2 | 11/2011 | Faram | |
| 9,114,224 B2 * | 8/2015 | Avni | A61M 16/0006 |
| 2002/0104535 A1 | 8/2002 | Biondo et al. | |
| 2005/0016530 A1 | 1/2005 | McCutcheon et al. | |
| 2005/0066968 A1 | 3/2005 | Shofner et al. | |
| 2008/0066754 A1 * | 3/2008 | Faram | A61M 16/0051 128/204.25 |
| 2008/0156319 A1 | 7/2008 | Avni | |
| 2008/0200848 A1 | 8/2008 | Avni | |
| 2009/0178672 A1 | 7/2009 | Mullinger et al. | |
| 2009/0306644 A1 | 12/2009 | Mayse et al. | |
| 2011/0180067 A1 | 7/2011 | Avni | |
| 2012/0247466 A1 | 10/2012 | Avni | |

OTHER PUBLICATIONS

Israeli Patent Office, "International Preliminary Report on Patentability dated Aug. 1, 2011 in corresponding International Application No. PCT/IL2009/000962", Aug. 1, 2011, Israel.

Koiwa et al., Modification of Human Left Ventricular Relaxation by Small-Amplitude, Phase-Controlled Mechanical Vibration on the Chest Wall, Circulation, 1997, pp. 156-162, vol. 95, American Heart Association, Inc.

Takagi et al., Diastolic vibration improves systolic function in cases of incomplete relaxation, Circulation, 1992, pp. 1955-1964, vol. 86, American Heart Association, Inc.

Nakayama et al., Benefit of in-phase chest wall vibration on the pulmonary hemodynamics in patients with chronic obstructive pulmonary disease, Respirology, Dec. 1998, pp. 235-240, vol. 3, No. 4.

Jiao et al., Effect of different vibration frequencies on heart rate variability and driving fatigue in healthy drivers, Int Arch Occup Environ Health, 2004, pp. 205-212, vol. 77.

* cited by examiner

MEANS AND METHOD FOR FLUID PULSES

CROSS-REFERENCE TO RELATED APPLICATIONS

This application is a Continuation-in-Part application of U.S. patent application Ser. No. 13/377,087, filed Jan. 13, 2012 (U.S. Pat. No. 9,114,224, granted Aug. 25, 2015) which claims priority from U.S. provisional patent application No. 62/006,292, filed Jun. 2, 2014. Both of the applications are hereby incorporated by reference in their entirety.

FIELD OF THE INVENTION

The present invention relates to devices and method for influencing the respiratory system and, more specifically, to inhalers providing a train of bipolar pneumatic pulses.

BACKGROUND OF THE INVENTION

US 20110180067 discloses an air delivery device (ADD) configured for applying fluid pressure pulses (FPP) to a mouth of a patient comprising: an air blower for applying an air flow to a pressure chamber via a first opening; an airflow occluding means (AOM) being in fluid communication with the pressure chamber located between the first opening and a second opening of the pressure chamber; a respiratory mask in fluid communication with said second opening and attachable to the mouth of the patient and applying the FPP at the mouth of the patient during inspiration and expiration of the patient. The AOM comprises a fixed disc and a rotary disc. The fixed disc and said rotary disc are cooperatively configured to interrupt and release said airflow at a predetermined variable frequency and pressure thereby generating the FPP according to a predetermined protocol during operation of the ADD.

The clinical trials performed by the Applicant have indicated that the best therapeutic effect is achievable when abrupt bipolar pneumatic pulses are applied to the patient's respiratory tract. Thus, there is a long felt unmet need for providing a patient with a compact personal device generating trains of the aforesaid abrupt bipolar pneumatic pulses effective in reopening airways and sustaining the achieved effect.

SUMMARY OF THE INVENTION

It is hence one object of the invention to disclose a pulsating therapeutic inhaler generating pneumatic pulses for treating respiratory disorders. The aforesaid inhaler comprises: (a) a linear passage having an elongate axis; the linear passage configured to conduct a fluid flow in a laminar manner; (b) a patient interface fluidly connectable to the patient's respiratory tract having an aperture fluidly connectable to the passage; and (c) a shutter disposed between the passage and the aperture configured to modulate a fluid pressure within the fluid flow; the shutter comprising a disc having at least one cutout and rotating about an axis parallel to the passage axis.

It is a core purpose of the invention to provide the cutout having four cornered perimeter thereof with two side portions and two circumferential arcs configured relative to the rotation axis. The side portions are circumferentially anti-symmetrical relative to the aperture.

Another object of the invention is to disclose the cutout and aperture which are identical and defined by circumferential arcs interconnected by radial segments.

A further object of the invention is to disclose the cutout having a variable circumferential dimension corresponding to a time profile of the fluid pressure pulses provided to the airways of a patient.

A further object of the invention is to disclose the inhaler comprising a source of fluid.

A further object of the invention is to disclose the fluid source selected from a group consisting of a turbine, a fluid vessel and any combination thereof.

A further object of the invention is to disclose the inhaler comprising means for varying aspiration resistance.

A further object of the invention is to disclose the inhaler comprising a dispenser configured to dispense a medicament into the fluid flow.

A further object of the invention is to disclose the inhaler providing a train of bipolar pneumatic pulses.

A further object of the invention is to disclose the rotating disc driven by a mover.

A further object of the invention is to disclose the mover selected from a group consisting of an electric motor, a driving spring, a turbine and any combination thereof.

A further object of the invention is to disclose the driving turbine coaxially integrated with the rotating disc.

A further object of the invention is to disclose a method of treating respiratory disorders by means of applying pneumatic pulses to the patient's respiratory tract. The aforesaid method comprises the steps of: (a) providing a pulsating inhaler further comprising (i) a linear passage having an elongate axis; the linear passage configured to conduct a fluid flow in a laminar manner; (ii) a patient's interface fluidly connectable to the patient's respiratory tract having an aperture fluidly connectable to the passage; and (iii) a shutter disposed between the passage and the aperture configured to modulate a fluid pressure within the fluid flow; the shutter comprising a disc having at least one cutout and rotating about an axis parallel to the passage axis; (b) fluidly connecting the patient interface to the patient's respiratory tract; (c) modulating the fluid pressure within the fluid flow by means of the shutter.

It is another core purpose of the invention to provide the step of modulating the fluid pressure performed by the cutout having four cornered perimeter thereof with two side portions and two circumferential arcs configured relative to the rotation axis; the side portions are circumferentially anti-symmetrical relative to the aperture.

A further object of the invention is to disclose the step of modulating the fluid pressure performed by the cutout and aperture which are identical and defined by circumferential arcs interconnected by radial segments.

A further object of the invention is to disclose a time profile of the fluid pressure pulses provided to the airways of a patient which is variable by means of change in a circumferential dimension of the cutout.

A further object of the invention is to disclose the method comprising a step of breath assisting by means of a source of fluid.

A further object of the invention is to disclose the method comprising a step of breath resistance training by of means for varying breath resistance.

A further object of the invention is to disclose the method comprising a step of dispensing a medicament into the fluid flow.

A further object of the invention is to disclose the step of modulating the fluid pressure which comprises providing a train of bipolar pneumatic pulses.

A further object of the invention is to disclose the step of modulating the fluid pressure performed by the rotating disc driven by a mover.

A further object of the invention is to disclose the bipolar pneumatic pulses characterized by amplitude ranging between 0.5 and 20 cm $H_2O$.

A further object of the invention is to disclose the bipolar pneumatic pulses characterized by pulse front tilt no greater than 30°.

A further object of the invention is to disclose a method of treating respiratory disorders by means of applying pneumatic pulses to the patient's respiratory tract. The aforesaid method comprises a step of modulating a fluid flow within the patient's respiratory tract.

It is another core purpose of the invention to provide modulated fluid flow obtained at said step of modulating said fluid flow comprises bipolar pneumatic pulses characterized by amplitude ranging between ±0.5 and ±50 cm $H_2O$ and pulse front tilt no greater than 30°.

BRIEF DESCRIPTION OF THE DRAWINGS

In order to understand the invention and to see how it may be implemented in practice, a plurality of embodiments is adapted to now be described, by way of non-limiting example only, with reference to the accompanying drawings, in which.

DETAILED DESCRIPTION OF THE INVENTION

The following description is provided, so as to enable any person skilled in the art to make use of said invention and sets forth the best modes contemplated by the inventor of carrying out this invention. Various modifications, however, are adapted to remain apparent to those skilled in the art, since the generic principles of the present invention have been defined specifically to provide means and method for providing fluid pulses.

Figure 1A:
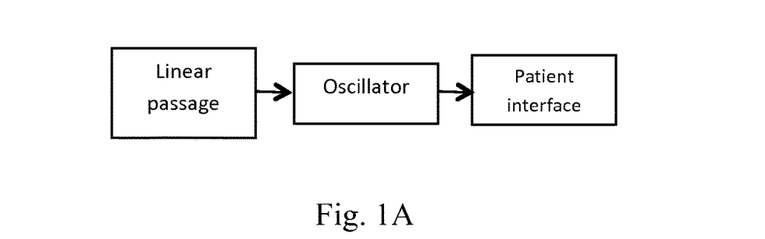
FIGS. 1A-1D are schematic diagrams of embodiments of a pulsating therapeutic inhaler.
Figure 1B:
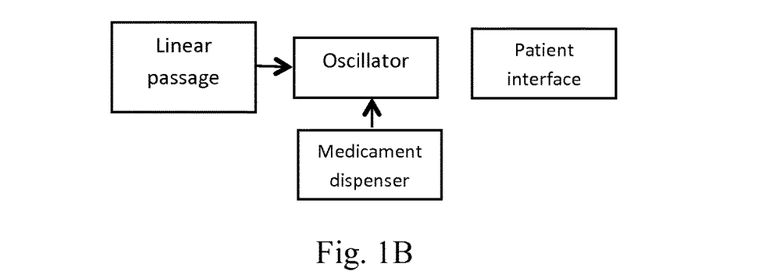

Reference is now made to FIGS. 1A-1D, presenting alternative embodiment of the present invention. Specifically, FIG. 1A shows a schematic diagram of a pulsating therapeutic inhaler according to its main embodiment. The inhaler comprises a linear passage configured for conducting a fluid flow in a laminar manner, an oscillator embodied as a disc shutter and a patient interface. FIG. 1B presents a schematic diagram of the pulsating therapeutic inhaler provided with a medicament dispenser. In the pulsating therapeutic inhalers of FIGS. 1A and 1B, air flow is propelled by patient's inhalation/exhalation.

Figure 1C:
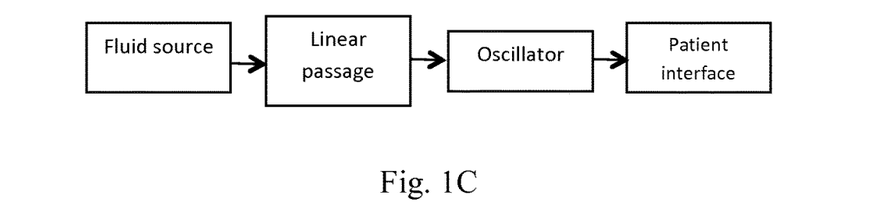

As described below, the oscillator can comprise, for example, a fluid turbine driven by inhalation/exhalation of the patient. An electric motor and a driving spring are also in the scope of the present invention. FIG. 1C presents an embodiment additionally comprising a fluid source providing an excessive pressure within the fluid passage. It should be emphasized that creation of underpressure within the fluid passage is also in scope of the present invention. An electrically driven fluid turbine and a vessel with pressurized fluid can be used as the fluid source. Underpressure can be created by means of reversing the aforesaid turbine.

Figure 1D:
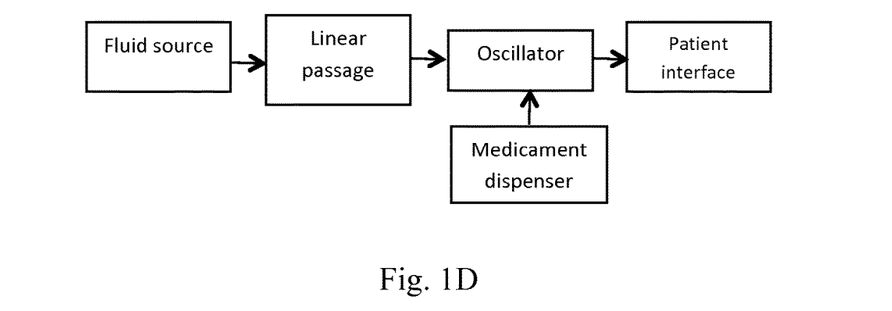

FIG. 1d depicts an embodiment including a combination of fluid turbine and a medicament dispenser. Powder and liquid medicaments are in the scope of the present invention.

Figure 2:
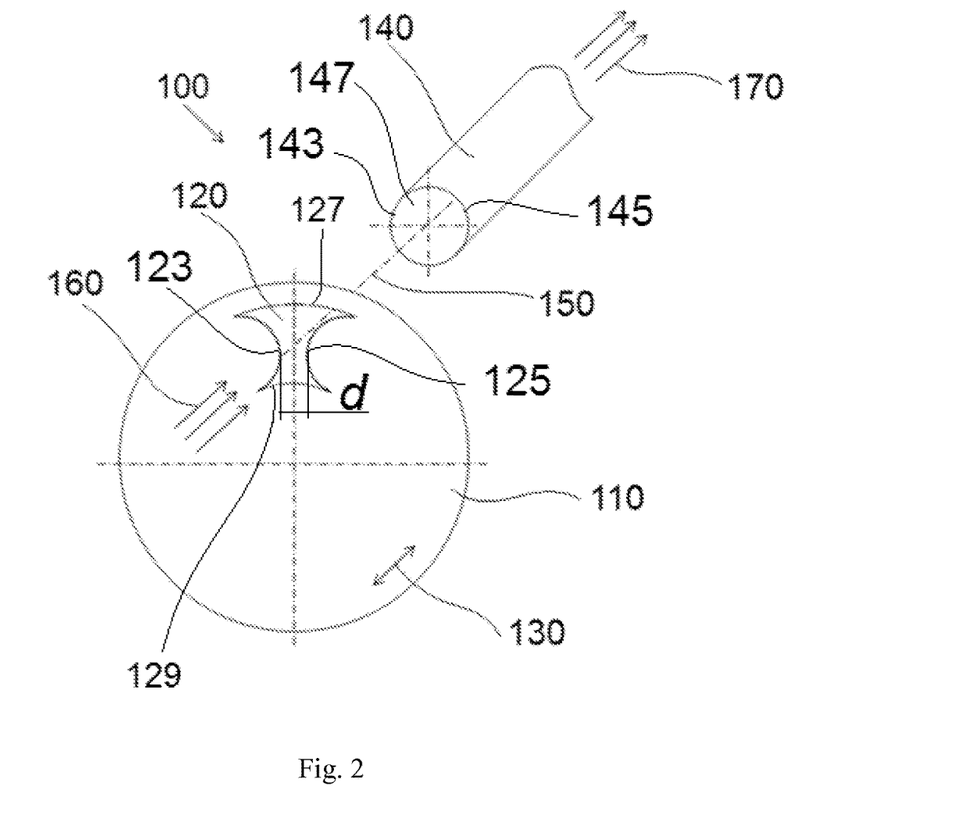
FIG. 2 is a prospective exploded view of a disc shutter including a round aperture and a disc provided with a cutout which is anti-symmetrical to the aperture shape.

Reference is now made to FIG. 2, presenting a prospective exploded view of a flat disc shutter including a round aperture of a patient interface and a disc provided with a cutout which is anti-symmetrical to the aperture shape. An arrangement 100 comprises a first embodiment of rotating disc 110 provided with a cutout 120. Numeral 130 refers to alternative rotation directions of the first rotating disc 110. A patient interface 140 has a round aperture 147. To achieve a maximum available steepness of generated pneumatic pulses, congruence between opposite side portions 123/125 of the cutout 120 and semi-circumferences 143/145 of the round aperture 147 should be provided. Specifically, the side portion 123 is congruent to the semi-circumference 145, while the portion 125 to the semi-circumference 143. Curvatures of side portion 123 is antisymmetric to semicircle 143 and side portion 125 is antisymmetric to semicircle 145. Circumferential perimeter portions 127 and 129 are radially configured and spaced apart at a distance which is equal to a diameter of the round aperture 147. According to a main embodiment of the present invention, a fluid enters into the arrangement 100 along arrows 160, flows along an axis 150 and exits along arrows 170.

A backward direction of the fluid flow corresponding, for example, to patient's exhalation is also in the scope of the present invention. Duration of a generated pneumatic pulse depends on a circumferential dimension d of the cutout 120.

Figure 3:
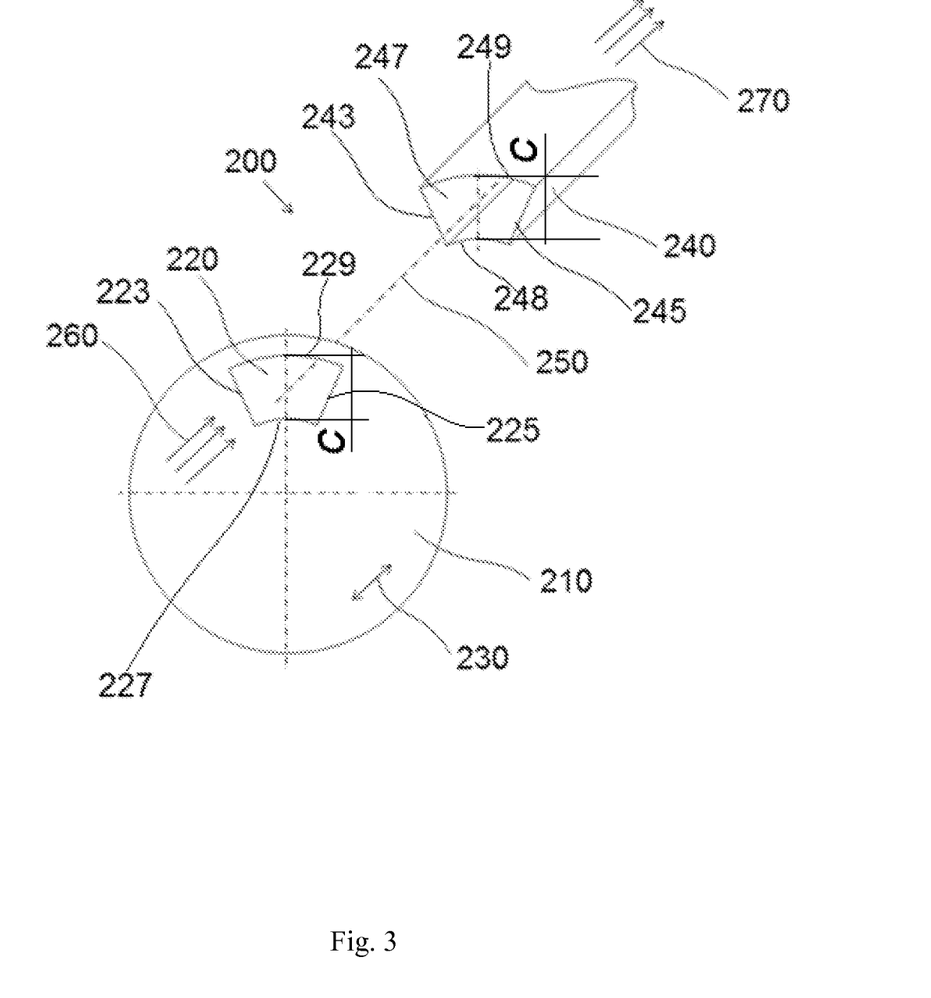
FIG. 3 is a prospective exploded view of a disc shutter including trapezoid aperture and disc cutout.

Reference is now made to FIG. 3, presenting a prospective exploded view of a disc shutter including a circular trapezoid aperture and a disc provided with a cutout congruent with the aforesaid circular trapezoid aperture. Specifically, an arrangement 200 comprises a second embodiment of rotating disc 210 provided a cutout 220 having side perimeter portions 223/225 and circumferential perimeter portions 227/229. Numeral 230 refers to alternative rotation directions of the second rotating disc 210. A patient interface 240 has a circular trapezoid aperture 247 congruent to the cutout 220. A perimeter of the trapezoid aperture 247 is defined by side portions 243/245 and circumferential perimeter portions 248/249. Radial distances c between perimeter portions 227/229 and 248/249 are equal.

Similar to the previous embodiment of the present invention, a fluid enters into the arrangement 200 along arrows 260, flows along an axis 250 and exits along arrows 270. A backward direction of the fluid flow is also optional.

Figure 4A:
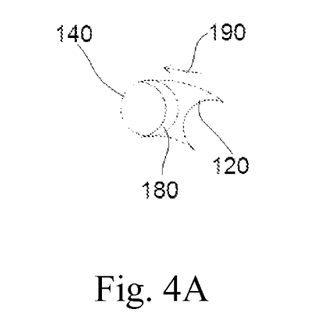
FIGS. 4A-4C illustrate gradual overlapping of a round aperture and an anti-symmetrical cutout within a rotating disc.
Figure 4B:
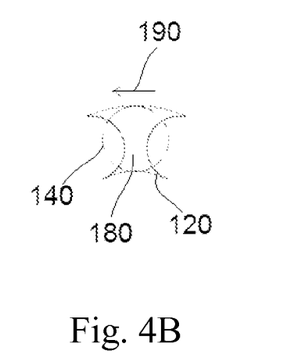
Figure 4C:
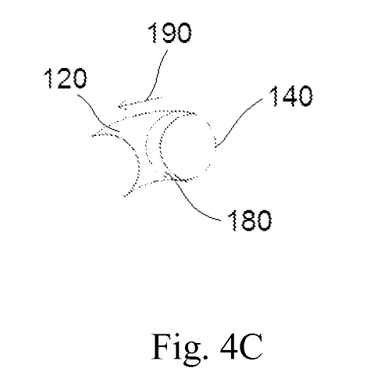

Reference is now made to FIGS. 4A-4C providing a gradual presentation of overlapping between the aperture 140 and the cutout 120. As mentioned above, maximum steepness of generated pneumatic pulses is achieved by means of congruence of opposite perimeter side portions of the aperture 140 and the cutout 120 which provides maximal increase/decrease rate of overlapping area 180. Numeral 190 refers to a direction of disc rotation.

Figure 5:
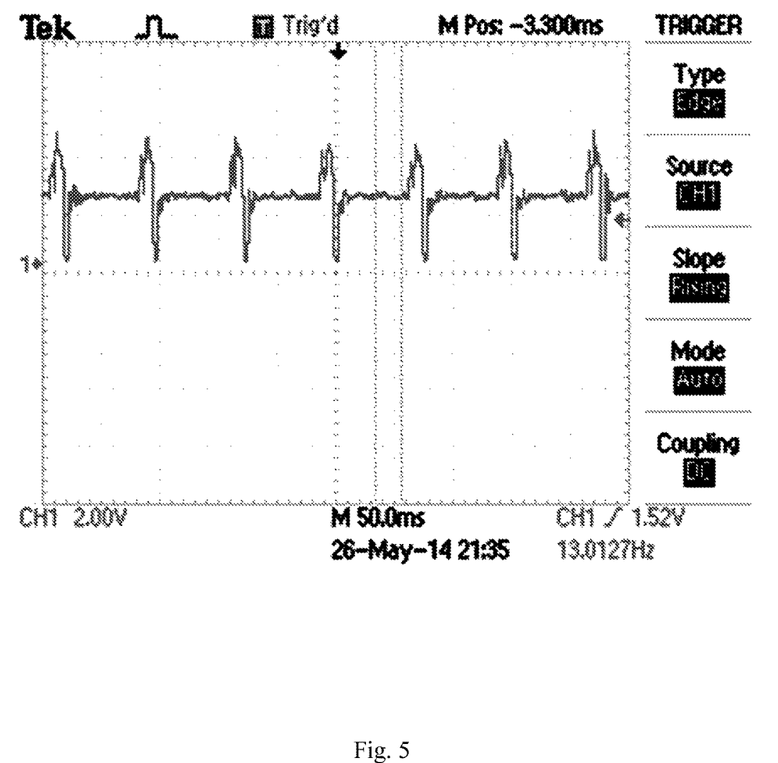
FIG. 5 is an experimental graph of a train of pneumatic pulses generated by a disc shutter.

Reference is now made to FIG. 5 presenting an experimental graph of time dependence of air pressure within the patient interface. The obtained pneumatic pulses are characterized by bipolar pattern, which is interpreted as creation of an underpressure area within the patient interface, when the disc shutter is closed. Natural diffusion quickly restores atmosphere pressure.

Figure 6A:
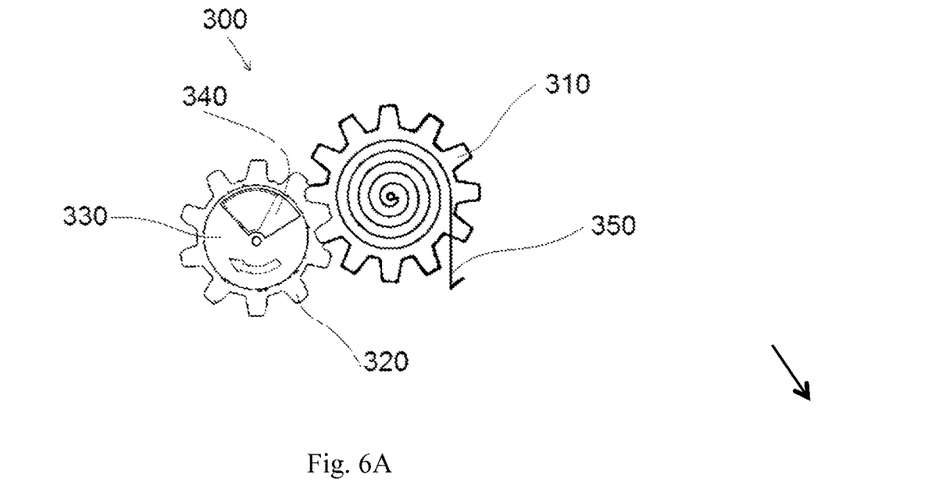
FIGS. 6A and 6B are schematic diagrams of a disc shutter driven by a driving spring.
Figure 6B:
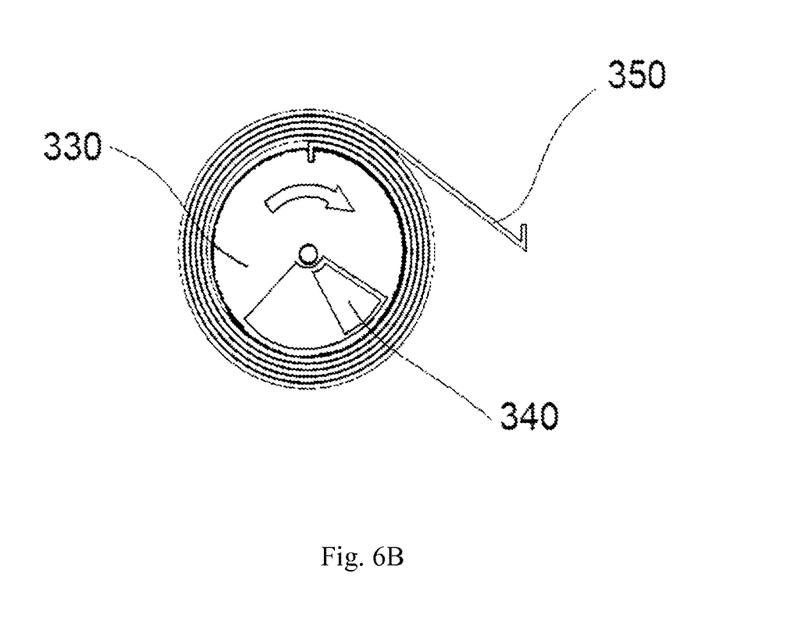

Reference is now made to FIGS. 6A and 6B, presenting two embodiments of the present invention. In FIG. 6A, an arrangement 300 comprises a third rotating disc 330 provided with a cutout 340 which is mounted on a cog wheel 320 coupled with a cog wheel 310 driven by a spring 350. According to another embodiment, the third embodiment of rotating disc 330 is driven by the spring 350 directly.

Figure 7A:
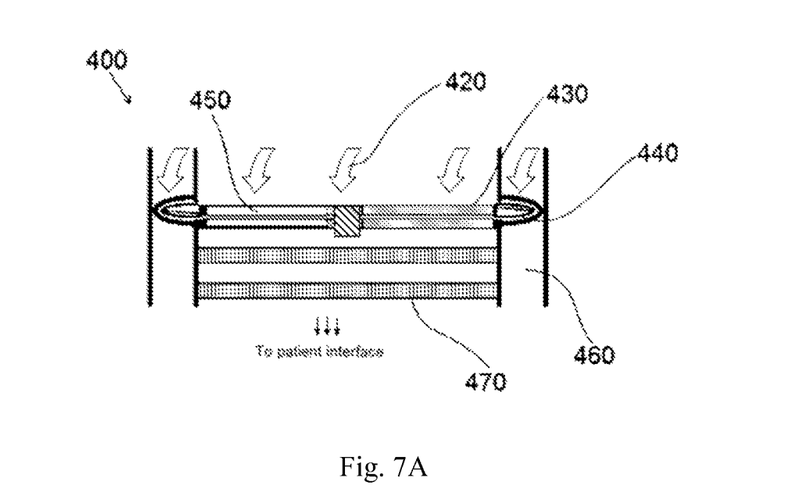
FIGS. 7A, 7B and 8 illustrate a coaxially configured arrangement including a disc shutter and a driving turbine.
Figure 7B:
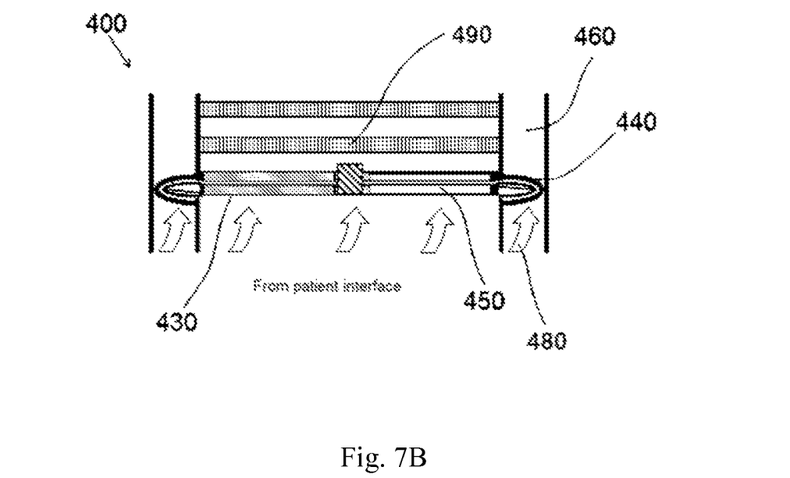
Figure 8:
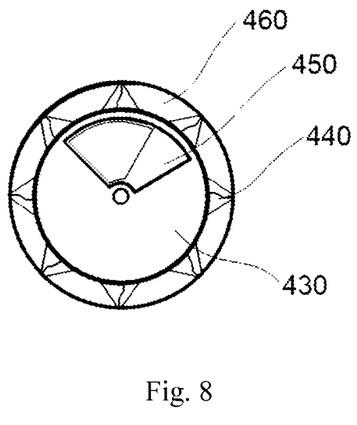

Reference is now made to FIGS. 7A, 7B and 8 presenting two embodiments of the present invention. In FIG. 7A, an arrangement 700 comprises a forth rotating disc 430 provided with cutout 450 mounted coaxially with a wheel 440 of a driving turbine. When a patient inhales, air partially flowing in a passage 460 propels the turbine wheel 440. Air 420 is modulated by the rotating disc 430 serving as a shuttering valve. Numeral 470 refers to a train of pneumatic pulses entering the patient interface (not shown). According to an alternative embodiment of the present invention (FIG. 7B), exhaled air 480 enters the arrangement 400. A therapeutic effect is achieved due to varying resistance to patient's exhale. Similar to the previous embodiment, air partially flowing in a passage 460 propels the turbine wheel 440. The forth embodiment of rotating disc 430 with the cutout 450 creates variable resistance to patient's exhale 480. Air exhausted from the arrangement 400 is signed by numeral 490.

Figure 9:
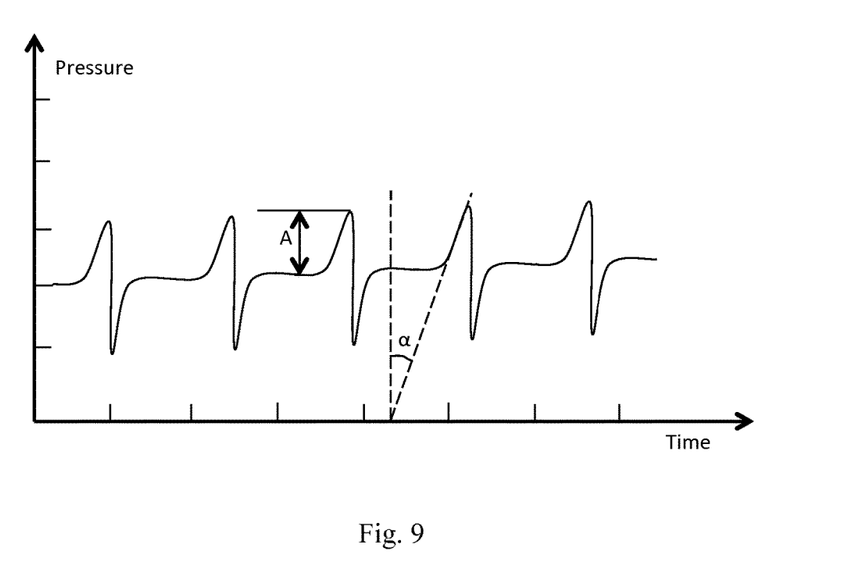
FIG. 9 is a graph of a time dependence of fluid pressure within a patient interface (constant turbine capacity)

Reference is now made to FIG. 9 presenting a graph a train of pneumatic pulses. Each pneumatic pulse is characterized by amplitude A and an angle of pulse front a. According to the present invention, an expected therapeutic effect is achieved at amplitude A ranging between ±0.5 and ±50 cm $H_2O$ and an angle of pulse front a no greater than 30°.

As mentioned above, the pneumatic pulses are characterized by bipolar pattern, which is interpreted as creation of an underpressure area, when the disc shutter is closed. It should be emphasized that the obtained bipolar pulses (combination of increased and decreased pressure areas) provides an additional synergetic effect in the treatment of respiratory disorders. Pulse frequencies ranging up to 500 Hz are in the scope of the present invention.

Figure 10:
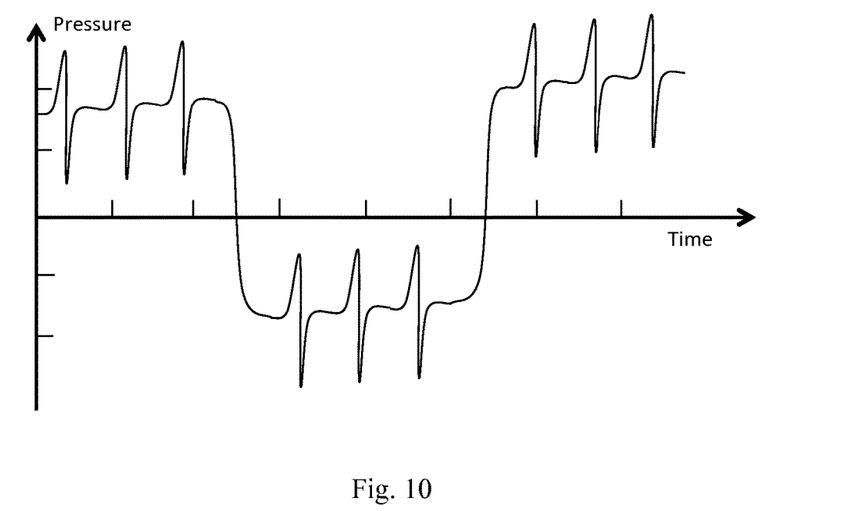
FIG. 10 is a graph of a time dependence of fluid pressure within a patient interface (bidirectional turbine)

Reference is now made to FIG. 10 presenting a graph a train of pneumatic pulses generated by a pulsating therapeutic inhaler provided with bidirectional turbine serving as a fluid source. Pulse chains with a mean line at excessive pressure and underpressure are provided into the patient interface in turns. A passive inhaler providing modulation inhale/exhale air flow is also in the scope of the present invention.

Figure 11:
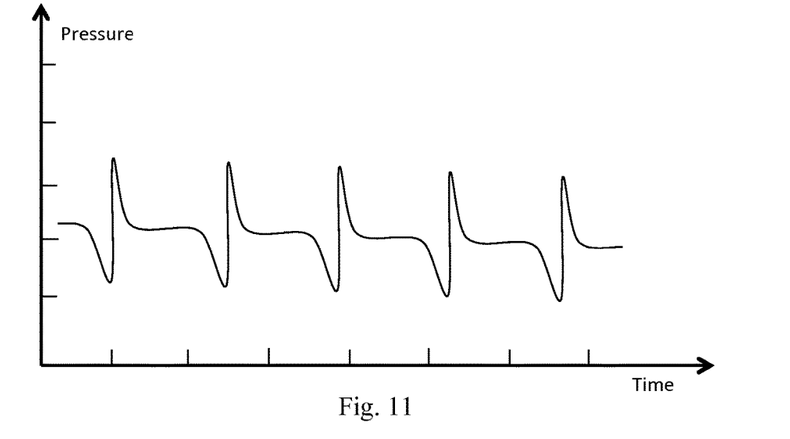
FIG. 11 is a graph of a time dependence of fluid pressure within a patient interface (shutter disc having missing parts)

Reference is now made to FIG. 11 presenting a graph a train of pneumatic pulses generated by a rotating disc having missing sectorial parts. According to this embodiment of the present invention, the disc shutter can be considered a normally-open valve. Therefore, at the moment of closing the air flow by a non-missing part of the rotating disc, an underpressure area is provided to the patient interface. After opening the shutter, an area of the excessive pressure is created within the patient interface.

Figure 12:
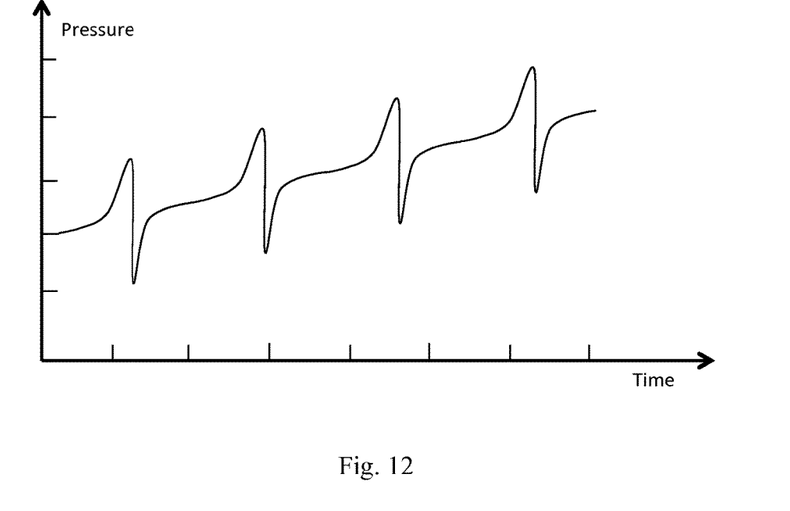
FIG. 12 is a graph of a time dependence of fluid pressure within a patient interface (exhalation)
Figure 13:
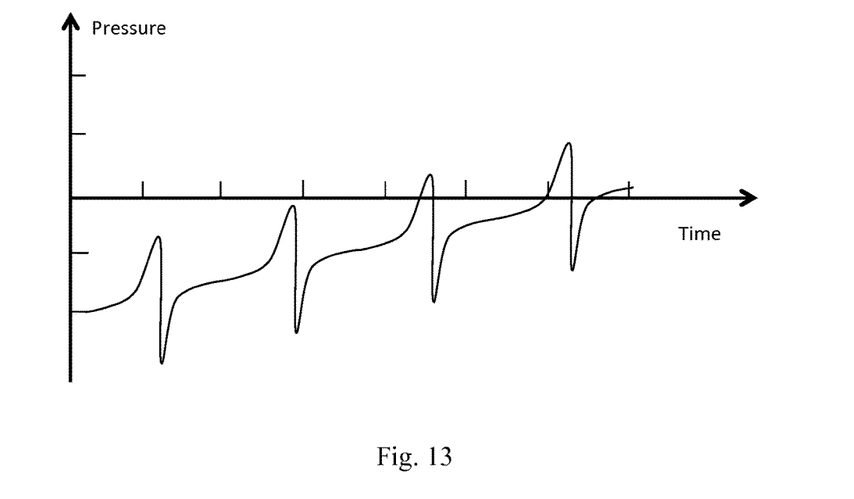
FIG. 13 is a graph of a time dependence of fluid pressure within a patient interface (inhalation).

Reference is now made to FIGS. 12 and 13, presenting breath patterns corresponding to exhalation and inhalation, respectively. Pneumatic pulse trains are imposed on natural air pressure within the patient's respiratory tract. During an exhalation phase, there is excessive pressure within the patient interface, while during the inhalation phase, an underpressure area is created.

In accordance with the present invention, a pulsating therapeutic inhaler generating pneumatic pulses for treating respiratory disorders is disclosed. The aforesaid inhaler comprises: (a) a linear passage having an elongate axis; the linear passage configured to conduct a fluid flow in a laminar manner; (b) a patient interface fluidly connectable to the patient's respiratory tract having an aperture fluidly connectable to the passage; and (c) a shutter disposed between the passage and the aperture configured to modulate a fluid pressure within the fluid flow; the shutter comprising a disc having at least one cutout and rotating about an axis parallel to the passage axis.

It is a core feature of the invention to provide the cutout having four cornered perimeter thereof with two side portions and two circumferential arcs configured relative to the rotation axis. The side portions are circumferentially anti-symmetrical relative to the aperture.

According to another embodiment of the present invention, the cutout and aperture are identical and defined by circumferential arcs interconnected by radial segments.

According to a further embodiment of the present invention, the cutout has a variable circumferential dimension corresponding to a time profile of the fluid pressure pulses provided to the airways of a patient.

According to a further embodiment of the present invention, the inhaler comprises a source of fluid.

According to a further embodiment of the present invention, the fluid source is selected from a group consisting of a turbine, a fluid vessel and any combination thereof.

According to a further embodiment of the present invention, the inhaler comprises means for varying aspiration resistance.

According to a further embodiment of the present invention, the inhaler comprises a dispenser configured to dispense a medicament into the fluid flow.

According to a further embodiment of the present invention, the inhaler provides a train of bipolar pneumatic pulses.

According to a further embodiment of the present invention, the rotating disc is driven by a mover.

According to a further embodiment of the present invention, the mover IS selected from a group consisting of an electric motor, a driving spring, a turbine and any combination thereof.

According to a further embodiment of the present invention, the driving turbine is coaxially integrated with the rotating disc.

According to a further embodiment of the present invention, a method of treating respiratory disorders by means of applying pneumatic pulses to the patient's respiratory tract is disclosed. The aforesaid method comprises the steps of: (a) providing a pulsating inhaler further comprising (i) a linear passage having an elongate axis; the linear passage configured to conduct a fluid flow in a laminar manner; (ii) a patient's interface fluidly connectable to the patient's respiratory tract having an aperture fluidly connectable to the passage; and (iii) a shutter disposed between the passage and the aperture configured to modulate a fluid pressure within the fluid flow; the shutter comprising a disc having at least one cutout and rotating about an axis parallel to the passage axis; (b) fluidly connecting the patient interface to the patient's respiratory tract; (c) modulating the fluid pressure within the fluid flow by means of the shutter.

It is another core feature of the invention to provide the step of modulating the fluid pressure performed by the cutout having four cornered perimeter thereof with two side portions and two circumferential arcs configured relative to the rotation axis; the side portions are circumferentially anti-symmetrical relative to the aperture.

According to a further embodiment of the present invention, the step of modulating the fluid pressure is performed by the cutout and aperture which are identical and defined by circumferential arcs interconnected by radial segments.

According to a further embodiment of the present invention, a time profile of the fluid pressure pulses provided to the airways of a patient is variable by means of change in a circumferential dimension of the cutout.

According to a further embodiment of the present invention, the method comprises a step of breath assisting by means of a source of fluid.

According to a further embodiment of the present invention, the method comprises a step of breath resistance training by of means for varying breath resistance.

According to a further embodiment of the present invention, the method comprises a step of dispensing a medicament into the fluid flow.

According to a further embodiment of the present invention, the step of modulating the fluid pressure comprises providing a train of bipolar pneumatic pulses.

According to a further embodiment of the present invention, the step of modulating the fluid pressure is performed by the rotating disc driven by a mover.

According to a further embodiment of the present invention, the bipolar pneumatic pulses are characterized by amplitude ranging between 0.5 and 20 cm $H_2O$.

According to a further embodiment of the present invention, bipolar pneumatic pulses are characterized by pulse front tilt no greater than 30°.

According to a further embodiment of the present invention, a method of treating respiratory disorders by means of applying pneumatic pulses to the patient's respiratory tract is disclosed. The aforesaid method comprises a step of modulating a fluid flow within the patient's respiratory tract.

It is another core feature of the invention to provide the modulated fluid flow obtained at said step of modulating said fluid flow which comprises bipolar pneumatic pulses characterized by amplitude ranging between ±0.5 and ±50 cm $H_2O$ and pulse front tilt no greater than 30°.

What is claimed is:

1. A pulsating therapeutic inhaler generating pneumatic pulses for treating respiratory disorders, said inhaler comprising:
    a. a linear passage having an elongate axis;
    b. a patient interface fluidly connectable to the patient's respiratory tract having a curvilinear aperture fluidly connectable to said linear passage; said curvilinear aperture selected from the group consisting of a circle and a circular trapezoid; and
    c. a flat shutter disposed between said linear passage and said aperture configured to modulate a fluid pressure within a fluid flow; said flat shutter comprising a disc (110) having at least one cutout (120) and rotating about an axis parallel to said elongate axis of said linear passage;
    said cutout has four cornered perimeter thereof with two radial side portions (123 and 125) and two circumferential arcs (127 and 129) configured relative to said rotation axis; said side portions are circumferentially anti-symmetrical relative to said aperture.

2. The inhaler according to claim 1, wherein said cutout and aperture are identical and defined by circumferential arcs interconnected by radial segments.

3. The inhaler according to claim 1, wherein said cutout has a variable circumferential dimension corresponding to a time profile of said fluid pressure pulses provided to the airways of a patient.

4. The inhaler according to claim 1 comprising a source of fluid.

5. The inhaler according to claim 4, wherein said fluid source is selected from a group consisting of a turbine, a fluid vessel and any combination thereof.

6. The inhaler according to claim 1 comprising a dispenser configured to dispense a medicament into said fluid flow.

7. The inhaler according to claim 1 providing a train of bipolar pneumatic pulses.

8. The inhaler according to claim 7, wherein said bipolar pneumatic pulses are characterized by amplitude ranging between ±0.5 and ±50 cm $H_2O$.

9. The inhaler according to claim 7, wherein said bipolar pneumatic pulses are characterized by pulse front tilt no greater than 30°.

10. The inhaler according to claim 1, wherein said disc is driven by a mover.

11. The inhaler according to claim 1, wherein said mover is selected from a group consisting of an electric motor, a driving spring, a turbine and any combination thereof.

12. The inhaler according to claim 11, wherein said turbine is coaxially integrated with said rotating disc.

13. A method of treating respiratory disorders by means of applying pneumatic pulses to the patient's respiratory tract; said method comprising the steps of:
    a. providing a pulsating inhaler further comprising
       i. a linear passage having an elongate axis;
       ii. a patient's interface fluidly connectable to the patient's respiratory tract having an aperture fluidly connectable to said linear passage; and
       iii. a flat shutter disposed between said linear passage and said aperture configured to modulate a fluid pressure within a fluid flow; said flat shutter comprising a disc having at least one cutout and rotating about an axis parallel to said elongate axis of said linear passage;
    b. fluidly connecting said patient interface to the patient's respiratory tract;
    c. modulating said fluid pressure within said fluid flow by means of said flat shutter;
        wherein said step of modulating said fluid pressure is performed by said cutout having four cornered perimeter thereof with two radial side portions and two circumferential arcs configured relative to said rotation axis; said side portions are circumferentially anti-symmetrical relative to said aperture.

14. The method according to claim 13, wherein said step of modulating said fluid pressure is performed by said cutout and aperture which are identical and defined by circumferential arcs interconnected by radial segments.

15. The method according to claim 13, wherein a time profile of said fluid pressure pulses provided to the airways of a patient is variable by means of change in a circumferential dimension of said cutout.

16. The method according to claim 13 comprising a step of breath assisting by means of a source of fluid.

17. The method according to claim 16, wherein said fluid source is selected from a group consisting of a turbine, a fluid vessel and any combination thereof.

18. The method according to claim 13 comprising a step of dispensing a medicament into said fluid flow.

19. The method according to claim 13, wherein said step of modulating said fluid pressure comprises providing a train of bipolar pneumatic pulses.

20. The method according to claim 19, wherein said bipolar pneumatic pulses are characterized by amplitude ranging between ±0.5 and ±50 cm $H_2O$.

21. The method according to claim 19, wherein said bipolar pneumatic pulses are characterized by pulse front tilt no greater than 30°.

22. The method according to claim 13, wherein said step of modulating said fluid pressure is performed by said disc driven by a mover.

23. The method according to claim 22, wherein said mover is selected from a group consisting of an electric motor, a driving spring, a turbine and any combination thereof.

24. The method according to claim 23, wherein said turbine is coaxially integrated with said rotating disc.

\* \* \* \* \*